United States Patent
Ahrens et al.

[11] 4,021,450
[45] May 3, 1977

[54] THIOPHENE DERIVATIVES AND THEIR PREPARATION

[75] Inventors: Hanns Ahrens; Helmut Biere; Clemens Rufer; Ralph Schmiechen; Eberhard Schroeder; Olaf Loge; Wolfgang Losert; Ekkehard Schillinger, all of Berlin, Germany

[73] Assignee: Schering Aktiengesellschaft, Berlin & Bergkamen, Germany

[22] Filed: May 20, 1975

[21] Appl. No.: 579,196

[30] Foreign Application Priority Data
May 21, 1974 Germany .......................... 2424740

[52] U.S. Cl. .................... 260/332.2 A; 260/329 S; 260/332.3 R; 260/332.5; 424/248.51; 424/275; 260/247.1 P
[51] Int. Cl.² ..................................... C07D 333/24
[58] Field of Search ..... 260/329 S, 332.5, 332.2 A, 260/332.3 R, 247.1

[56] References Cited
UNITED STATES PATENTS
2,581,626  1/1952  Brooks ..................... 260/332.2 A

*Primary Examiner*—Bernard Helfin
*Assistant Examiner*—A. Siegel
*Attorney, Agent, or Firm*—Millen & White

[57] ABSTRACT

Thiophene derivatives of the formula

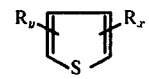

wherein $R_x$ is —S-CHR$_5$-COOH or -S-CH$_2$-CH$_2$-OH, $R_y$ is 1-2 of halogen alkoxy of 1-6 carbon atoms, aralkyl of 7-10 carbon atoms, phenyl, halophenyl or alkylcarbonyl of 1-6 carbon atoms in the alkyl group, and $R_5$ is a hydrogen atom, when $R_y$ is a halogen atom, when $R_5$ is alkyl, their enantiomers, and their pharmacologically acceptable salts thereof with bases, possess antilipolytic activity.

11 Claims, No Drawings

THIOPHENE DERIVATIVES AND THEIR PREPARATION

BACKGROUND OF THE INVENTION

This invention relates to novel, antilipolytically active thiophene derivatives and to process for the preparation and use thereof.

Pathologically high blood serum concentrations of triglycerides are held responsible, inter alia, for the origination and progression of arteriosclerotic changes of the blood vessel wall. The triglycerides in the serum originate not only from food intake but also from the liver, where they are synthesized from the blood, in part with the use of free fatty acids (FFA). A lowering of the FFA content in the serum results in a lowering of the triglyceride condentration in the liver and in the blood. BIZZI, VENERONI, and GARATTINI, J. Pharm. Pharmac. 18, 611, 1966; PAOLETTI and PUGLIST, Naunyl-Schmeidebergs Arch. Pharmak., 269, 317, 1971.

Since the FFA concentration in the serum depends primarily on the extent to which the triglyceride is split in the fatty tissue (lipolysis), a pharmacological inhibition of this process represent an effective measure for lowering the triglyceride level in the serum and to prevent arteriosclerotic changes of blood vessels. This was proven by animal experiments. BIZZI, VENERONI, and GARATTINI, J. Pharm. Pharmac. 18, 611, 1966; BIZZI, GARATTINI, VENERONI, HOWARD, GRESHAM, and JENNINGS, Atherosclerosis, in print, 1974. Also in humans, a reduction of the triglyceride concentration in the serum was measured after treatment with agents which inhibit lipolysis. BERINGER, BAENDER, GLANINGER, MAYRHOFER, and SCHNAK, Horm. Metab. Res. 2, 81, 1970.

Moreover, a reduction in the FFA concentration in the serum by lipolysis inhibition in the fatty tissue is also a sensible therapeutic principle for the treatment of diabetes mellitus. In accordance with invenstigations conducted by RANDLE and collaborators (RANDLE, P. J. in B. S. LEIBEL and G. A. WRENSHALL, Editors: On the Nature and Treatment of Diabetes, Excerpta Medica Foundation, Amsterdam-New York-London-Milan-Tokyo Buenos Aires, p. 361, 1965), FFA's interfere with the utilization of glucose for the purpose of obtaining energy in the periphery of the body (musculature). Glucose absorption into the muscle cells is a process dependent on insulin. Since insulin simultaneously inhibits lipolysis and thus the transfer of FFA from the fatty tissue of the blood, the glucose utilization in the body periphery is disturbed for a dual reason in diabetes mellitus, which is characterized by restricted insulin secretion and production.

Primarily, the lack of insulin leads to a disturbance in the glucose absorption by the muscle cells. This disturbance is aggravated by the simultaneously increase in the FFA concentration in the blood and the concomitant, increased FFA fed to the body periphery. This factor is eliminated when lipolysis in the fatty tissue is pharmacologically inhibited; glucose utilization is improved and elevated blood glucose concentration is lowered. This has been shown in experiments on rats with insulin deficiency. FROESCH, WALDVOGEL, MEYER, JAKOB, and LABHART, Mol. Pharmacology, 3, 442, 1967. It can be confirmed in diabetics by improved glucose tolerance, a lowering of elevated blood glucose levels and a reduction of glucose in the urine. In this connection, agents inhibiting lipolysis either proved to be effective in monotherapy or were capable of again normalizing the defective carbohydrate metabolism in secondary failures of therapy with $\beta$-cytotropic sulfonyl ureas and/or sulfonyl ureas and biguanides, in combination with these medicines. BERINGER, BAENDER, GLANINGER, MAYRHOFER, and SCHNACK, Horm. Metab. Res., 2, 81, 1970; GEYER and SOKOPP, Vienna, "Klin. Wschr." 81, 701, 1969; GEYER and SOKOPP, "Med. u. Ernaehr." 10, 115, 1969; NEUMANN, MICHAELIS, BIBERGEIL, and WULFERT, "Dtsch. Ges. Wesen" 27, 972, 1972.

Compounds heretofore used in such investigations as agents for inhibiting lipolysis, such as nicotinic acid, 3-pyridinemethanol, 5-(3-pyridyl)-tetrazole, 3,5-dimethylpyrazole, 3,5-dimethylisoxazole; the active metabolites 5-methylpyrazole-3-carboxylic acid and 5-methylisoxazole-3-carboxylic acid, formed in the organism from the two last-mentioned compounds; various other pyrazole and isoxazole derivatives; as well as a number of adenosine derivatives, effect an initial lowering of serum FFA. However, they cannot be employed for a long-term therapy of metabolic anomalies, for various reasons. Except for the adenosine derivatives, all above-mentioned compounds, especially nicotinic acid and compounds derived therefrom, after diminution of their FFA-lowering activity, result in an increase of free fatty acids in the serum, overshooting the initial level (rebound phenomenon), thus nullifying the positive consequences of their initial effect. BIZZI and GARATTINI in: Metabolic Effects of Nicotinic Acid and Its Derivatives, Hans-Huber publishers, Berne, p. 207, 1971. Moreover, pyrazole and isoxazole derivatives, as well as pyridyltetrazole, lose their lipolysis-inhibiting capacity repeated application on successive days, after a shorter or longer period of time, and thus lose their ability to lower the concentration of FFA in the serum. This behavior, called tachyphylaxis, was observed in animal experiments. BIZZI and GARATTINI in: Metabolic Effects of Nicotinic Acid and Its Derivatives, Hans-Huber publishers, Berne, 1971, p. 207; FROESCH, WALDVOGEL, MEYER, JAKOB, and LABHART, Mol. Pharmacol. 3, 442, 1967; SCHILLINGER and LOGE, Biochem. Pharmacol., in print, 1974. It was confirmed in man made during the clinical application of 5-methylpyrazole-3-carboxylic acid and 5-methylisozazole-3acid. NEUMANN, MICHAELIS, BIBERGEIL, and WULFERT, "Dtsch. Ges. Wesen" 27 972, 1972; GEYER and SOKOPP, Acta endocr. (Kbh.) Suppl. 173, 127, 1973. In accordance with the above-mentioned findings, the phenomenon of tachyphylaxis need not necessarily be related to the rebound phenomenon but, just as the latter, the former phenomenon is prohibitive for long term therapy.

Antilipolytically effective adenosine derivatives exhibit neither a rise in serum FFA, overshooting the starting level, after the initial reduction, nor a loss in effectiveness upon repeated administration. SCHILLINGER and LODGE, Biochem. Pharmacol., in print, 1974. However these compounds possess only an extremely small therapeutic range, since they affect cardiac activity at lipolytically effective or only slightly higher doses, and lead to a drop in the heartbeat frequency. MANNESMANN, publication in preparation, 1974. Due to this dangerous effect on the cardiovascular system, adenosine derivatives cannot be used in long-term therapy in humans.

In the search for lipolysis-inhibiting agents suitable for a long-term administration to humans, it has been found, surprisingly, that the novel thiophene derivatives of this invention exhibit neither the phenomenon of tachyphylaxis nor that of overshooting the free fatty acid level after an initial reduction (rebound phenomenon). Moreover, no effect on heartbeat frequency was seen and the therapeutic dosage range is very wide.

SUMMARY OF THE INVENTION

In a composition aspect, this invention relates to thiophene derivatives of the general Formula I wherein one of $R_1$, $R_2$, $R_3$ and $R_4$ is $R_x$; 1 or 2 thereof are $R_y$; and the remainder are hydrogen atoms; wherein $R_y$ is a halogen atom, alkoxy of 1-6 carbon atoms, aralkyl of 7-10 carbon atoms, phenyl, phenyl substituted by one or more halogen atoms, or alkylcarbonyl of 1-6 carbon atoms in the alkyl group, and wherein $R_x$ is $$-S-\overset{R_5}{\underset{|}{CH}}-COOH \text{ or } -S-CH_2-CH_2-OH,$$

$R_5$ being a hydrogen atom when $R_y$ is a halogen atom, including, when $R_5$ is alkyl, their enantiomers, and their pharmacologically acceptable salts with inorganic and organic bases.

In another composition, this invention relates to pharmaceutical compositions comprising a compound of this invention in admixture with a pharmaceutically acceptable carrier.

In process aspects, this invention relates to processes for the production and use as antilipolytic agents of the compounds of this invention.

In this aspect (5-alkyl-2-thienylthio)-acetic acid derivatives are known from the literature [S. Gronowitz Arkiv Kemi 20, 297 (1963); S. Gronowitz Acta Pharm Suecica 2, 65 (1965); O. Dann, Chem. Ber. 87, 373 (1954); YA. L. Goldfarb Zh. Obschej Chim. 29, 363 (1959)], but in only one citation are these derivatives proposed for use in central nervous system diseases and in any case without any disclosure regarding an antilipolytic activity.

DETAILED DISCUSSION

Specifically contemplated classes of compounds of this invention include those wherein:

a. $R_x$ is $-S-CHR_5-COOH$, especially those wherein $R_1$ is $R_x$;

b. $R_x$ is $-S-CH_2-CH_2-OH$, especially wherein $R_1$ is $R_x$;

c. those of (a) wherein $R_5$ is H or $CH_3$, preferably H;

d. those of (a), (b) and (c) wherein 2 of $R_1$, $R_2$, $R_3$ and $R_4$ are H;

e. those of (a), (b) and (c) wherein 1 of $R_1$, $R_2$, $R_3$ and $R_4$ are H;

f. those of (a), (b), (c), (d) and (e) wherein an $R_y$ is at the 5- position, especially those wherein the $R_y$ at the 5- position is $CH_3O$, $C_2H_5O$, $C_3H_7O$, Cl, Br, phenyl, benzyl or halophenyl;

g. those of (a), (b), (c), (d) and (e) wherein an $R_y$ is bromo;

h. those of (a) as a pharmaceutically acceptable salt with a base, preferably an organic base, especially methylglucamine.

The alkyl groups can be straight-chain or branched and saturated or unsaturated. Specific examples are methyl, ethyl, n-propyl, isopropyl, n-butyl, isobutyl, tert.-butyl, n-pentyl, n-hexyl groups, preferred being alkyl of 1-4 carbon atoms, which preferably are straight-chain.

The alkyl groups in the alkoxy groups correspond to the above alkyl groups. Specific examples are n-propoxy, isopropoxy, n-butoxy, isobutoxy, tert.-butoxy, n-pentoxy, n-hexyloxy, and the preferred methoxy and ethoxy.

The aralkyl groups of 7-10 carbon atoms are preferably benzyl or phenylethyl.

The halogen atoms include fluorine and iodine atoms, but preferably bromine and chlorine atoms.

The pharmacologically acceptable salts of this invention include salts of both inorganic and organic bases, and are those customarily employed by those skilled in the art for the salt formation. Examples of suitable bases are sodium hydroxide, potassium hydroxide, calcium hydroxide, magnesium hydroxide, glucamine, N-methylglucamine, N,N-dimethylglucamine, ethanolamine, diethanolamine, 2-amino-2-hydroxymethyl-1,3-propanediol and morpholine.

In a process aspect, this invention relates to processes for the production of thiophene derivatives of general Formula I and their salts with basis, wherein: a compound of general Formula II wherein one of $R_1'$, $R_2'$, $R_3'$ and $R_4'$ is a $-S-H-$ group, 1 or 2 thereof are $R_y$ and the remainder hydrogen atoms, or an alkali metal salt of the thiol, a. is reacted, to produce compounds of general Formula I wherein $R_x$ is $-S-CHR_5-COOH$, with a halogen compound of the general Formula III $$X - CHR_5-COOR_6$$

wherein $R_5$ has the values given above; X is a halogen atom; and $R_6$ is a hydrogen atom or alkyl of 1-4 carbon atoms, and the thus-obtained compounds wherein $R_6$ is alkyl are thereafter saponified; or b. is reacted, to produce compounds of general Formula I wherein $R_x$ is $-S-CH_2-CH_2-OH$, with a halogen alcohol of the general Formula IV $$X - CH_2 - CH_2 - OH$$

wherein X has the above values given, and optionally thereafter, the compound of Formula I obtained according to (a) or (b), respectively, is subjected to a racemate splitting step and/or is converted with a base into a pharmacologically acceptable salt.

Alkali salts of the thiols of general Formula III include sodium and potassium salts but preferably are lithium salts.

Preferred halogen atoms in the halogen compounds of general Formulae III and IV are chlorine and bromine.

The reaction of the thiol or of an alkali salt thereof with a halogen ester of the general Formula III ($R_6$ = alkyl) according to procedure (a) or with a halogen alcohol of the general Formula IV according to procedure (b) is conducted in the presence of an inert organic solvent, preferably an ether, such as, for example, diethyl ether or tetrahydrofuran. The halogen ester is added at a temperature of from −70° C to 0° C, preferably about −20° C. After the ester has been added, the reaction mixture is agitated for several hours at temperatures of from room temperature to the boiling point of the solvent employed.

The thienylthio ester obtained as described above is saponified under conventional conditions, preferably with sodium hydroxide in an alcoholic solution.

The reaction of a thiol or an alkali salt thereof with a halocarboxylic acid of general Formula III ($R_6$ = H) is conducted in an aqueous-alkaline solution at temperatures of from 0° C to 60° C, preferably 20° C to 40° C.

If products are obtained during the course of the process which contain an asymmetrical carbon atom, the primarily obtained racemic acids can optionally be separated into their optically active enantiometers in accordance with known methods. Suitably, the racemic acid is converted into its salt with an optically active base, and the optically active forms are separated by fractional crystallization. After the separation has been accomplished, the optically active acid is liberated from the salt in the usual manner. Preferred as optically active bases are brucine, strychnine, α-phenylethylamine, α-naphthylethylamine, and similar compounds.

The thiols or the alkali salts thereof utilized as the starting materials are either known from the literature or can be prepared according to methods known in the literature.

It is especially advantageous to lithiate a correspondingly substituted thiophene derivative with butyllithium and then convert the product with sulfur into the thiol. This process has the advantage that the thiol, obtained as its lithium salt, need not be isolated, but rather can be further processed immediately.

The novel compounds of this invention are suitable for the lowering of the free fatty acid levels in the blood plasma of animals and humans, including long range therapy without incurring, after an initial reduction, a rise which exceeds original values and without undesired and/or damaging effects on the cardiovascular system. The compounds thus can be used for the treatment of metabolic diseases, such as, for example, diabetes mellitus, hyperlipemia, and arteriosclerosis. In the treatment of diabetes mellitus, this treatment possibility can be made as a fourth possibility of equivalent value to the three customary drug therapies, viz., insulin, sulfonylamino compounds and biguanides.

The compounds of this invention have special significance in combination therapy with the medicinal agents conventionally utilized in the treatment of diabetes mellitus. In the tables below; the effects obtained with one of the compounds of this invention is compared with those obtained with a known compound as standard, viz., 5-methylisoxazole-3-carboxylic acid and 5-methylpyrazole-3-carboxylic acid, respectively, in their "one-day profile" of FFA reduction (after one-time administration) and in their profile of FFA reduction after daily administration for several days ("tachyphylaxis profile").

The compounds of this invention significantly reduce, after one-time oral administration, the free fatty acids (FFA) in the serum of fasting rats, as can be seen from Table A using as an example of a compound of this invention, (5-methoxy-2-thienylthio)acetic acid, and as comparison compound to the conventional 5-methylpyrazole-3-carboxylic acid. In the compound of this invention, an initial lowering of the FFA content is not followed by the undesirable resumption of the increase in FFA observed after treatment with 5-methylpyrazole-3-carboxylic acid. This "rebound" phenomenon, also observed in other conventional lipolysis-inhibiting agents, is independent of dosage and nullifies the positive results of the initial reduction and renders the therapeutic value of such a compound doubtful.

Table B illustrates the antilipolytic effect of (5-methoxy-2-thienylthio)-acetic acid after treatment for several days. The compound shows, after a period of five days, i.e., at a point in time where the reference compound 5-methylisoxazole-3-carboxylic acid no longer reduces FFA, unchanged antilipolytic activity. This lack of tachyphylactic effects, which is characteristic of compounds of this invention, is an absolute prerequisite for the long-term administration of a lipolysis-inhibiting agent.

The novel effective agents can be administered orally or parenterally. The processing into forms of application can be accomplished without additives or together with the additives, vehicles, flavor-ameliorating agents, and others customary in galenic pharmacy, namely for example in powder form, as tablets, dragees, capsules, pills, in the form of suspensions or solutions.

The amount of active agent to be administered can range between 1 and 100 mg./kg., preferably between 1 and 30 mg./kg. body weight per day. Dosage units can contain 10 mg. to 1 g. of active agent, preferably 50–550 mg. of active agent.

TABLE A

One-day profile of the free fatty acids (FFA) in the serum of fats fasting for 24 hours after oral treatment with (5-methoxy-2-thienylthio)-acetic acid (I) and 5-methylpyrazole-3-carboxylic acid (II) as compred to the untreated control group (III).
Average Values of 10 Animals:

| FFA After (Hours) | FFA in meq./l. After I, 10 mg./kg. | II, 5 mg./kg. | Control III |
|---|---|---|---|
| 0 | 1.082 | 1.247 | 0.974 |
| 1 | 0.622 | 0.289 | 0.866 |
| 2 | 0.623 | 0.317 | 0.808 |
| 4 | 0.643 | 0.486 | 0.931 |
| 7 | 0.641 | 1.076 | 0.832 |
| 9 | 0.573 | 1.172 | 0.828 |
| 14 | 0.846 | 1.334 | 1.244 |
| 19 | 0.941 | 1.003 | 0.896 |
| 24 | 0.664 | 0.788 | 0.826 |

―――: Significantly different from the control group.

TABLE B

FFA-Lowering effect of (5-methoxy-2-thienylthio)-acetic acid (I) and 5-methylisoxazole-3-carboxylic acid (II) as compared to the untreated control group (III) on the first and fifth days of oral treatment of rats fasting for 24 hours (tachyphylaxis test).

| | | FFA in meq./l. Serum Day 1 | Day 5 |
|---|---|---|---|
| I | (10 mg./kg.) | 0.63 | 0.58 |
| II | (1 mg./kg.) | 0.41 | 0.72 |
| III | Control | 0.85 | 0.80 |

―――: Significantly different from the control group.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

(5-Methoxy-2-thienylthio)-acetic Acid

At −20°, 92 ml. (204 millimoles) of approximately 22% butyllithium solution (in hexane) is added dropwise to 23.3 g. (204 millimoles) of 2-methoxythiophene in 100 ml. of anhydrous ether. The apparatus is purged with dry nitrogen. The mixture is allowed to warm up to room temperature, maintained at room temperature for one hour, cooled to −40°, and within 15 minutes 6.6 g. (204 millimoles) of sublimed sulfur is added thereto by way of a solids metering funnel. The mixture is then kept for 30 minutes at 0° and for 30 minutes at room temperature. Thereafter, the mixture is poured into 200 ml. of ice water, the organic supernatent phase is separated, extracted once with 50 ml. of water, and the combined aqueous solutions are added under agitation to a sodium chloroacetate solution previously produced from 20.8 g. (204 millimoles) of chloroacetic acid and 14.1 g. (102 millimoles) of potash in 150 ml. of water. The mixture is stirred overnight at room temperature, extracted twice with respectively 100 ml. of ether, and the aqueous-alkaline phase is combined with concentrated hydrochloric acid to pH 1. The thus-separated, brown oil is extracted with ether (3 × 150 ml.). The ether is washed twice with respectively 150 ml. of water, dried over sodium sulfate, and concentrated. Distillation (b.p.$_{0.001}$: 127°) yields a slightly yellow oil which is still contaminated with traces of chloroacetic acid. The distillation product is maintained, for removing the chloroacetic acid, for 3 hours on a forced circulation evaporator at an oil pump vacuum and at a bath temperature of 70°, and then allowed to stand for crystallizing purposes.

M.p.: 68°–69° (from hexane); yield; 57% of theory.

EXAMPLE 2

(3-Methoxy-2-thienylthio)-acetic Acid

The compound is produced analogously to Example 1 from 3-methoxythiphene, butyllithium sulfur, and bromoacetic acid.

The crude product is distilled (b.p.$_{0.08}$: 135°–146°), and the distillate is crystallized after allowing the mixture to stand for several days at room temperature.

M.p.: 53°–54° (carbon tetrachloride); yield: 32% of theory.

EXAMPLE 3

(5-Propoxy-2-thienylthio)-acetic Acid

The compound is prepared analogously to Example 1 from 2-propoxythiophene, butyllithium, sulfur, and chloroacetic acid.

The acid can be distilled even under an oil pump vacuum only with decomposition. The crude product is freed of traces of impurities by filtration over a silica gel column (eluent: hexane/acetone/formic acid = 84 : 15 : 1).

The NMR and IR data coincide with the indicated structure.

EXAMPLE 4

(5-Phenyl-2-thienylthio)-acetic Acid

This compound is produced analogously to Example 1 from 2-phenylthiophene (b.p.$_{0.7}$: 74°–78°), butyllithium, sulfur, and chloroacetic acid.

M.p.: 116°–118° (acetonitrile); yield: 60% of theory.

2-Phenylthiophene is produced from thiophene and aniline according to a method known from the literature.

EXAMPLE 5

[5-(p-Chlorophenyl)-2-thienylthio]-acetic Acid

The compound is prepared in accordance with Example 1 from 5-p-chlorophenylthiophene (m.p. 85°–86°), butyllithium, sulfur, and chloroacetic acid. In a modification of Example 1, 100 ml. of tetrahydrofuran is used as the solvent in place of ether for the charge of 50 millimoles. The crude product must be purified by chromatography on silica gel (eluent: cyclohexane/acetone/formic acid = 85 : 13.5 : 1.5). The crude product obtained by evaporation is recrystallized once from propanol − water.

M.p.: 115° (propanol - water); yield: 15% of theory.

5-p-Chlorophenylthiophene is prepared in accordance with a method known from the literature from p-chloroaniline and thiophene.

EXAMPLE 6

(5-Benzyl-2-thienylthio)-acetic Acid

This compound is produced analogously to Example 1 from 2-benzylthiophene (b.p.$_{26}$: 150°), butyllithium, sulfur, and chloroacetic acid. The crude product is maintained in a bulb tube apparatus at a bath temperature of 120° and under an oil pump vacuum for 5 hours to remove entrained chloroacetic acid, and then is distilled by means of the bulb tube at 1 . 10$^{-3}$ torr [mm. Hg] and at a heating bath temperature of 230°. A slightly yellow, highly viscous oil is thus obtained, the NMR and IR data of which coincide with the indicated structure.

Yield: 44% of theory.

EXAMPLE 7

(5-Bromo-2-thienylthio)-acetic Acid

The compound is prepared as described in Example 1 from 2,5-dibromothiophene, butyllithium, sulfur, and chloroacetic acid. The ether phase obtained after acidification is, after washing and drying, partially decolorized with active carbon and then concentrated. The slightly greenish oil, showing only traces of impurities by thin-layer chromatography, which decomposed during a separately conducted attempt at distillation at 0.01 torr, is taken up in the same volume of carbon tetrachloride and filtered over a column packed with a mixture of active carbon and kieselguhr (per 9.0 g. of crude acid in 9.0 ml. of carbon tetrachloride, a mixture of 20 g. of active carbon and 10 g. of kieselguhr is utilized which, after mounting of the compound, is eluted with 150 ml. of carbon tetrachloride). The eluate does not show any impurities in the thin-layer chromatogram. The oily carboxylic acid remaining after evaporation of the carbon tetrachloride is dried at 50° and under an oil pump vacuum and crystallized when left to stand for several days under cooling.

M.p.: 34°–35° (squeezed on clay); yield: 43% of theory.

EXAMPLE 8

(4-Bromo-3-thienylthio)-acetic Acid

While purging the apparatus with dry nitrogen, 24.2 g. (100 mmol) of 3,4-dibromothiophene in 50 ml. of dry ether is combined at −60° with 46 ml. (approximately 100 mmol) of about 22% butyllithium solution (in hexane) and maintained for 10 minutes at −60°. At −60° to −70°, the mixture is combined with 3.2 g. (100 mmol) of well-dried sublimed sulfur and agitated at this temperature for 45 minutes. Then, 12.25 g. (100 mmol) of ethyl chloroacetate in 50 ml. of ether is added dropwise at −70°, the mixture is maintained at room temperature for 30 minutes, and then introduced into a mixture of 250 g. of ice and 100 ml. of 5 N HCl. The mixture is extracted three times with respectively 100 ml. of ether, the ether is washed three times with respectively 80 ml. of saturated sodium bicarbonate solution and three times with respectively 50 ml. of saturated NaCl solution, and the ether extract is dried over $CaSO_4$, concentrated, and distilled. The ethyl ester of (4-bromo-3-thienylthio)-acetic acid is obtained as an oil in a 49% yield (b.p.$_{0.7}$:143°).

For purposes of saponification, 14.06 g. (50 mmol) of the ethyl ester of (4-bromo-3-thienylthio)-acetic acid is refluxed for 1 ½ hours with a small excess of 1 N NaOH (51 ml.) and 50 ml. of methanol. The solution is combined with 50 ml. of water, the alcohol distilled off, and the remaining aqueous-alkaline phase is extracted three times with respectively 50 ml. of ethyl acetate, acidified with 6 N HCl to pH 3, and again extracted three times with respectively 70 ml. of ethyl acetate. The ethyl acetate extracts obtained from the acidified solution are extracted three times with respectively 50 ml. of saturated sodium chloride solution, dried over $CaSO_4$, and evaporated; during this step, (4-bromo-3-thienylthio)-acetic acid is separated as a crystalline monohydrate.

M.p.: 92° (acetonitrile — water); yield: 83% of theory, calculated on the basis of the ester utilized for the saponification.

EXAMPLE 9

(5-Chloro-2-thienylthio)-acetic Acid

This compound is prepared analogously to Example 8 from the methyl ester of (5-chloro-2-thienylthio)-acetic acid used as the raw material for the saponification.

B.p.$_{0.1}$: 136° (yellow oil).

Yield: 45% of theory, based on the ester used for the saponification.

EXAMPLE 10

(4-Bromo-2-thienylthio)-acetic Acid

Analogously to Example 8, 2,4-dibromothiophene is metalized with butyllithium at −50° and then, after sulfur treatment, reacted with methyl chloroacetate to the methyl ester of (4-bromo-2-thienylthio)-acetic acid (83% yield); the latter is saponified in the form of the crude product. The mixture thus obtained is worked up analogously to Example 8, yielding a crude product which is purified by chromatography on silica gel (eluent: hexane/acetone/formic acid = 96 : 5 : 1). The (4-bromo-2-thienylthio)-acetic acid, which is pure as determined by thin-layer chromatography, is an oil which does not crystallize, yielding the physicochemical data to be expected and correct elementary analyses (C, H, S, Br).

EXAMPLE 11

(3-Bromo-2-thienylthio)-acetic Acid

The compound is prepared analogously to Example 10 by saponification of the crude methyl ester of (3-bromo-2-thienylthio)-acetic acid prepared with a 76% yield from 2,3-dibromothiophene, butyllithium, sulfur, and methyl chloroacetate. After chromatography on silica gel (eluent: hexane/acetone/acetic acid = 93 : 5 : 2), the product is obtained as a non-crystallizing oil. The compound shows the physicochemical data to be expected (IR, NMR spectrum) and yields correct elementary analysis for C, H, S, and Br.

EXAMPLE 12

(3,5-Dibromo-2-thienylthio)-acetic Acid Example

Analogously to Example 8, the methyl ester of (3,5-dibromo-2-thienylthio)-acetic acid is prepared from 2,3,5-tribromothiophene, butyllithim, sulfur, and methyl chloroacetate; this product is obtained with a 32% yield as an oily crude substance. The carboxylic acid is obtained readily by saponification of the ester analogously to Examfple 8.

M.p.: 83° (glacial acetic acid/water); yield: 90% of theory.

EXAMPLE 13

[5-(1-Oxopentyl)-2-thienylthio]-acetic Acid

At −20° and under nitrogen purging, 100 ml. (about 230 mmol) of approximately 22% butyllithium solution (in hexane) is added dropwise to 20.3 g. (130 mmol) of thiophene-2-carboxylic acid dimethylamide in 150 ml. of ether. The reaction mixture is allowed to reach room temperature, cooled to −60° after two hours of agitation, and 7.04 g. (220 mmol) of sulfur is added in incremental portions. After one hour of stirring at room temperature, the mixture is poured into 400 ml. of ice water, the organic phase is separated, washed twice with respectively 75 ml. of water, and the combined aqueous-alkaline phases are added to a solution of 20.8 g. (220 mmol) of chloroacetic acid and 15.2 g. (110 mol) of potassium carbonate in 150 ml. of water. The mixture is agitated overnight, extracted once with ether, and the aqueous phase is combined with concentrated HCl to pH 3 and then extracted with ether. The ether extracts are washed twice with water, dried over sodium sulfate, and concentrated. The thus-obtained brown oil is dried by means of an oil pump at 50° and is partially crystallized by allowing the product to stand overnight.

The crystals are vacuum-filtered and recrystallized from ethyl acetate/hexane.

M.p.: 56°–57° (from ethyl acetate/hexane); yield: 6% of theory.

Thiophene-2-carboxylic acid dimethylamide is produced from thiophene-2-carboxylic acid chloride and 40% dimethylamine solution.

B.p.$_{16}$: 151°–152°; yield: 62% of theory.

EXAMPLE 14

2-(3-Methoxy-2-thienylthio)-ethanol

The compound is produced analogously to Example 1 from 11.4 g. (100 mmol) of 3-methoxythiophene, 45.5 ml. (about 100 mmol) of about 22% butyllithium solution (in hexane), 3.2 g. (100 mmol) of sulfur, and 8.05 g. (100 mmol) of chloroethanol. Bulb tube distillation at 0.04 torr (bath temperature: 118°–129°) yields the alcohol as a slightly yellow oil.

EXAMPLE 15

(3,4-Dimethoxy-2-thienylthio)-acetic Acid

This compound is prepared and analogously to Example 1 from 3,4-dimethoxythiophene, butyllithium, sulfur, and chloroacetic acid, thus obtaining a slightly brownish oil which is crystallized when allowed to stand.

M.p.: 79°–81° (squeezed on clay); yield: 19% of theory.

3,4-Dimethoxythiophene is prepared in accordance with TURNBULL, U.S. Pat. No. 2,453,103.

B.p.$_{15}$: 140° bath temperature (bulb tube distillation).

EXAMPLE 16

2-[(5-Methoxy)-2-thienylthio]-propionic Acid

This compound is prepared analogously to Example 1 from 2-methoxythiophene, butyllithium, sulfur, and α-bromopropionic acid.

The slightly yellow oil, boiling at b.p.$_{0.05}$ = 144°–151° crystallizes when left to stand under cooling.

M.p.: 43°–45° (squeezed on clay); yield: 61% of theory.

EXAMPLE 17

(2,5-Dimethoxy-3-thienylthio)-acetic Acid

This compound is prepared analogously to Example 1 from 2,5-dimethoxythiophene, butyllithium sulfur, and bromoacetic acid.

Yield: 9% of theory.

2,5-dimethoxythiophene (b.p.$_{13}$: 83°–84°) is prepared according to a method known from the literature from 2,5-diiodothiophene and sodium methylate.

EXAMPLE 18

Methylglucamine Salt of (5-Methoxy-2-thienylthio)acetic Acid

A mixture of 204 mg. (1 mmol) of the carboxylic acid and 195 mg. (1 mmol) of N-methylglucamine in 5 ml. of ethanol is briefly heated to the boiling point and then cooled off.

M.p.: 126°–128° (from ethanol); yield: 95% of theory.

EXAMPLE 19

500 g. of (5-methoxy-2-thienylthio)-acetic acid, 3 g. of disperse silicic acid ("Aerosil"), and 47 g. of corn starch are screened, mixed homogeneously, and filled into hard gelatin capsules having a net filling of 550 mg./capsule.

EXAMPLE 20

500 g. of (5-methoxy-2-thienylthio)-acetic acid, 3 g. of disperse silicic acid ("Aerosil"), 45 g. of corn starch, 50 g. of dry binder cellulose ("Avicel PH 101"), and 2 g. of magnesium stearate are mixed homogenously and compressed into tablets in the usual manner on a tabletting press, each tablet weighing 600 mg. The tablets are thereafter provided with a coating lacquer consisting of 8 parts of hydroxypropylcellulose ("Klucel LF"), one part of castor oil, and one part of talc.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A thiophene derivative of the formula

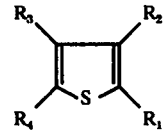

wherein one of $R_1$, $R_2$, $R_3$ and $R_4$ is $R_x$; 1 or 2 thereof are $R_y$ and the remainder thereof are hydrogen atoms, wherein $R_y$ is alkoxy of 1–6 carbon atoms, and wherein $R_x$ is -S-CH$_2$-COOH or -S-CH(CH$_3$)-COOH their enantiomers, and their pharmacologically acceptable salts thereof with bases.

2. A compound of claim 1 wherein $R_y$ is methoxy.

3. A compound of claim 1 wherein only 1 of $R_1$, $R_2$, $R_3$ and $R_4$ is $R_y$.

4. A compound of claim 2 wherein only 1 of $R_1$, $R_2$, $R_3$ and $R_4$ is $R_y$.

5. A compound of claim 4 wherein $R_4$ is $R_y$.

6. A compound of claim 1, (5-methoxy-2-thienylthio) acetic acid.

7. A compound of claim 1, (3-methoxy-2-thienylthio) acetic acid.

8. A compound of claim 1, (5-propoxy-2-thienylthio) acetic acid.

9. A compound of claim 1, (3,4-dimethoxy-2-thienylthio) acetic acid.

10. A compound of claim 1, 2-(5-methoxy-2-thienylthio)-2-methyl acetic acid.

11. A compound of claim 1, (2,5-dimethoxy-3-thienylthio) acetic acid.

* * * * *